United States Patent
Bonnard et al.

(10) Patent No.: US 11,043,096 B2
(45) Date of Patent: Jun. 22, 2021

(54) METHOD FOR DETECTING AN ELECTRICAL FAULT, DEVICE FOR IMPLEMENTING SUCH A METHOD AND ELECTRICAL ENCLOSURE EQUIPPED WITH SUCH A DEVICE

(71) Applicant: Schneider Electric Industries SAS, Rueil-Malmaison (FR)

(72) Inventors: Frederic Bonnard, Istres (FR); Daniel Moustrou, Istres (FR); Emir Boumediene, Grenoble (FR); Yannick Neyret, Biviers (FR)

(73) Assignee: Schneider Electric Industries SAS, Rueil-Malmaison (FR)

( * ) Notice: Subject to any disclaimer, the term of this patent is extended or adjusted under 35 U.S.C. 154(b) by 96 days.

(21) Appl. No.: 16/221,653

(22) Filed: Dec. 17, 2018

(65) Prior Publication Data
US 2019/0221095 A1 Jul. 18, 2019

(30) Foreign Application Priority Data
Jan. 16, 2018 (FR) .................... 18 50336

(51) Int. Cl.
| | |
|---|---|
| G08B 17/117 | (2006.01) |
| H02B 1/28 | (2006.01) |
| G01N 33/00 | (2006.01) |
| G08B 21/18 | (2006.01) |
| G08B 29/18 | (2006.01) |

(52) U.S. Cl.
CPC ....... *G08B 17/117* (2013.01); *G01N 33/0047* (2013.01); *G08B 21/182* (2013.01); *H02B 1/28* (2013.01); *G08B 29/185* (2013.01)

(58) Field of Classification Search
CPC .. G08B 17/117; G08B 21/182; G08B 29/185; G01N 33/0047; H02B 1/28
USPC ........................................ 340/632
See application file for complete search history.

(56) References Cited

U.S. PATENT DOCUMENTS

| | | | |
|---|---|---|---|
| 6,672,129 B1 * | 1/2004 | Frederickson | A61M 15/02 347/20 |
| 2015/0068287 A1 * | 3/2015 | Wilcox | G01M 3/04 73/40.5 R |
| 2017/0352242 A1 * | 12/2017 | Glynn | G08B 21/0469 |

(Continued)

FOREIGN PATENT DOCUMENTS

| | | |
|---|---|---|
| FR | 2 509 922 A1 | 1/1983 |
| WO | WO 2010/043272 A1 | 4/2010 |

OTHER PUBLICATIONS

French Preliminary Search Report dated Sep. 19, 2018 in French Application 18 50336, filed on Jan. 16, 2018 (with English Translation of Categories of Cited Documents & Written Opinion).

*Primary Examiner* — Jack K Wang
(74) *Attorney, Agent, or Firm* — Oblon, McClelland, Maier & Neustadt, L.L.P.

(57) ABSTRACT

A method for detecting a fault with electrical hardware installed in an enclosure. The method includes a step of measuring the concentration of volatile organic compounds, of microparticles and of gases. The measurements are corrected on the basis of climate data and then calculations of drift and change of concentration are performed. An alarm is emitted when a set of drift or change of concentration thresholds are crossed. A device implementing the method and to an electrical enclosure equipped with such a device.

11 Claims, 7 Drawing Sheets

(56) References Cited

U.S. PATENT DOCUMENTS

| | | |
|---|---|---|
| 2017/0372597 A1 | 12/2017 | Saintellemy et al. |
| 2018/0154297 A1* | 6/2018 | Maletich .............. B01D 46/442 |
| 2019/0294136 A1* | 9/2019 | Iacobone ........... G05B 19/0428 |
| 2020/0025706 A1* | 1/2020 | Yu ....................... G01N 27/403 |

* cited by examiner

METHOD FOR DETECTING AN ELECTRICAL FAULT, DEVICE FOR IMPLEMENTING SUCH A METHOD AND ELECTRICAL ENCLOSURE EQUIPPED WITH SUCH A DEVICE

TECHNICAL FIELD

The present invention relates to a method for detecting a fault in an electrical enclosure such as an electrical panel or enclosure. The invention also relates to a device for detecting a fault in an electrical enclosure and to an electrical enclosure equipped with such a device.

PRIOR ART

Currently, more and more sensors are used to provide information relating to the quality of breathing air or even for detecting potentially dangerous smoke in the event of an outbreak of fire. This type of information is useful in electrical installations where the operator sometimes perceives an abnormal temperature rise long before the appearance of any visible manifestation.

Document U.S. Pat. No. 6,317,053 B1 discloses an ambient air-tight electrical enclosure intended to contain computer hardware and comprising an early fire detection device. The device comprises fire detectors placed in the vicinity of a hot air extraction fan. Any detection of temperature rises by one of the sensors triggers the injection of an inert gas into the electrical enclosure. This device has the disadvantage of forcing the air in the electrical enclosure to pass through a pipe in order to be able to detect an outbreak of fire. Moreover, such a device does not need to be discriminating, the normal operation of the computer hardware does not generate any pollution that could be understood to be the result of combustion.

Document EP 1768074 A1 discloses a device for swift fire detection using a smoke or particles sensor, a temperature sensor and a sensor for measuring the speed of the airflow around the fire detection device. Monitoring the speed of the airflow allows a fire to be detected more quickly than with a conventional fire sensor. However, the device can generate a false alarm if the air is moved by a fan, for example.

Document WO 2010/043272 discloses a multi-function detector used for building management. It comprises multiple sensors intended to analyse the air quality in the building. The document cites, among other things, sensors for gases (carbon dioxide, ozone, nitrogen oxide) comprising flammable gases (propane, butane, methane, natural gas), sensors for particles, smoke, flammable particles, asbestos, mites or spores. The detector emits an alarm in the event of the detection of a situation that is harmful to the health of the occupants.

Other documents disclose solutions for avoiding the recurrent problem of false fire alarms. Document EP 0660282 B1 discloses a fire warning system using fuzzy logic processing of the data originating from the sensors. Document EP 0141987 B1 discloses a device that proceeds with a confirmation of the indications of a detector after two time intervals and an initial state reset of the indicator.

However, a device does not exist for detecting a fault originating from an abnormal temperature rise of electrical hardware in order to generate an early warning.

DISCLOSURE OF THE INVENTION

The present invention proposes a method for detecting the emanation of characteristic components associated with an abnormal temperature rise inside an electrical enclosure. Specific processing, based on several types of measurements, allows early and reliable detection of an operating anomaly characterized by an abnormal temperature rise, even when located in the vicinity of heat-emitting hardware.

To this end, the invention relates to a method for detecting a fault in an electrical enclosure comprising at least one electrical equipment item and at least one volatile organic compounds sensor, at least one microparticles sensor, at least one gas sensor, said method over time cyclically comprising:
  measuring at least one climate parameter in the electrical enclosure;
  measuring a concentration of volatile organic compounds;
  measuring a concentration of gases;
  measuring a concentration of microparticles;
  correcting the measurements of the concentration of volatile organic compounds, of gases and of microparticles on the basis of the at least one climate parameter;
  calculating a drift of concentration of volatile organic compounds, of gases and of microparticles on the basis of time;
  comparing the drift of concentration of volatile organic compounds, of gases and of microparticles, respectively, to a predefined drift of concentration threshold of volatile organic compounds, of gases and of microparticles;
  calculating a change of concentration of volatile organic compounds, of gases and of microparticles;
  comparing the change of concentration of volatile organic compounds, of gases and of microparticles, respectively, to a predefined change of concentration threshold of volatile organic compounds, of gases and of microparticles;
  emitting an alarm when:
  the drift of concentration of microparticles threshold or the change of concentration of microparticles threshold is exceeded; and when
  at least one drift of concentration threshold or one change of concentration threshold of volatile organic compounds or of gases is exceeded.

Preferably, calculating a drift of concentration of volatile organic compounds, of gases and of microparticles comprises:
  calculating a running mean, over a long period, of the concentration of volatile organic compounds, of gases and of microparticles;
  calculating a running mean, over a short period, of the concentration of volatile organic compounds, of gases and of microparticles;
  calculating a ratio respectively between the running mean over the short period and the running mean over the long period.

Preferably, the short period is between 15 and 60 minutes and the long period is between 5 and 12 hours.

Preferably, calculating a change of concentration, respectively, of volatile organic compounds, of gases and of microparticles comprises at least one calculation of the difference between two consecutive measurements of the concentration, respectively, of volatile organic compounds, of gases and of microparticles.

The invention also relates to a device for detecting an electrical fault comprising:
  at least one sensor for supplying a signal characteristic of the concentration of volatile organic compounds;
  at least one sensor for supplying a signal characteristic of the concentration of microparticles;

at least one sensor for supplying a signal characteristic of the concentration of gases;

at least one climate parameter sensor for supplying a value of at least one climate parameter;

a measurement circuit for measuring the signals supplied by the sensors;

an alarm circuit for generating an alarm; and a processing unit comprising circuits for executing the method for detecting a fault as previously described and for activating the alarm circuit when:

the drift of concentration threshold of microparticles or the change of concentration threshold of microparticles is exceeded; and when at least one drift of concentration or change of concentration threshold of volatile organic compounds or of gases is exceeded.

Preferably, the gas sensor supplies a signal characterizing a concentration of ammonia.

Preferably, the gas sensor supplies a signal characterizing a concentration of ozone.

Preferably, the organic volatile compounds sensor supplies a signal characterizing a concentration of hydrocarbons.

Preferably, the climate parameter sensor supplies a signal characterizing a temperature in the electrical enclosure.

Preferably, the climate parameter sensor also supplies a signal characterizing humidity in the electrical enclosure.

The invention also relates to an electrical enclosure comprising at least one cable or one electrical equipment item and to a device for detecting an electrical fault as previously described.

BRIEF DESCRIPTION OF THE DRAWINGS

Further advantages and features of the invention will become more clearly apparent from the following description of particular embodiments of the invention, which are provided by way of non-limiting examples, and are shown with reference to the accompanying drawings, in which.

DETAILED DESCRIPTION OF PREFERRED EMBODIMENTS

Figure 1:
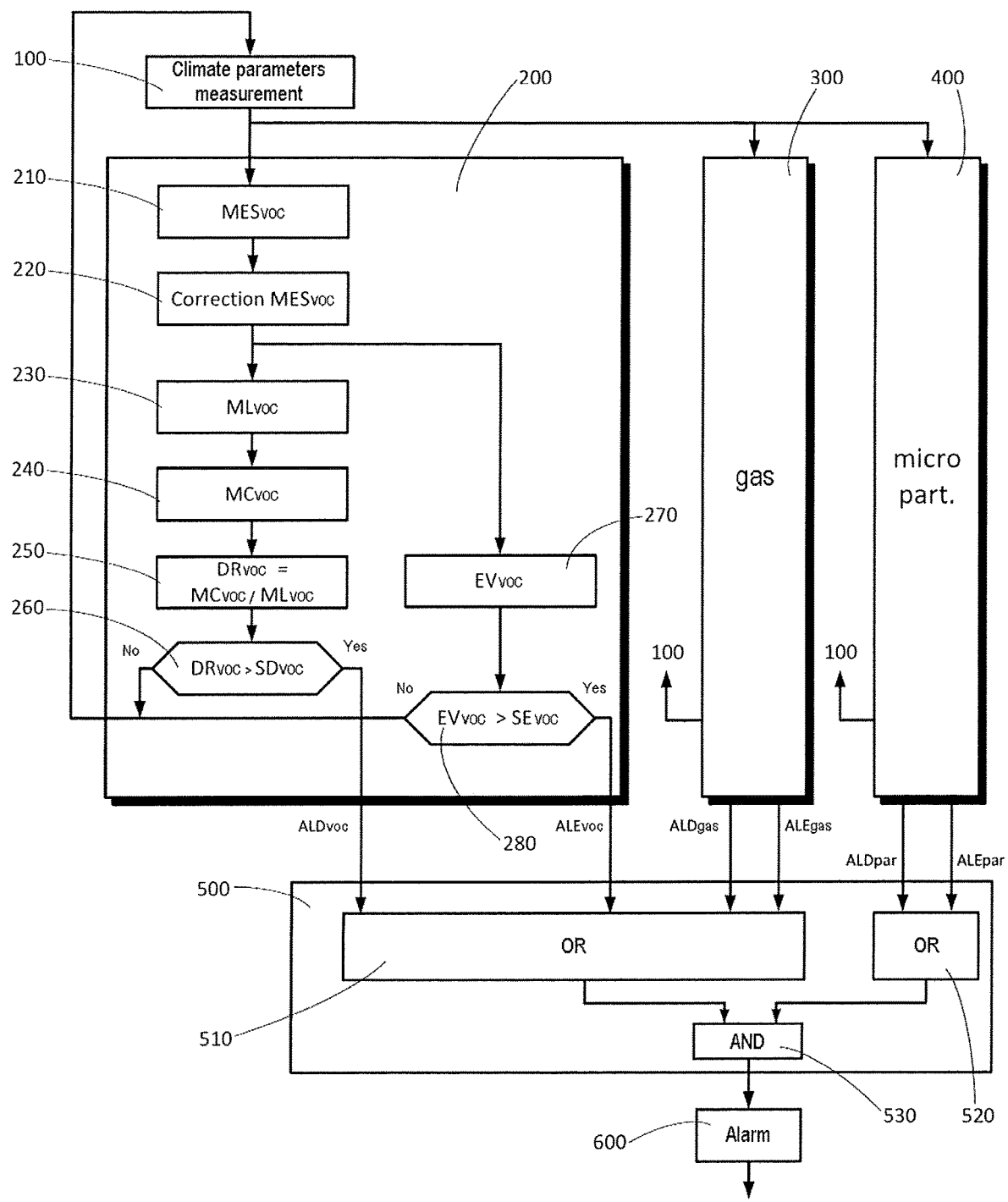
FIG. 1 shows a flow chart of a method for detecting a fault on the basis of measurements of climate conditions and of measurements of the concentration of volatile organic compounds, of microparticles and of gases according to the invention.

FIG. 1 shows a method for detecting a fault in an electrical enclosure 10 in the form of a flow chart. A measurement of at least one climate parameter in the electrical enclosure 10 is performed during a step 100. Preferably, two climate parameters are measured: the temperature T and the humidity H. Other climate parameters can be measured, for example, the atmospheric pressure P. Measuring at least one of these climate parameters is required to correct the measurements performed by the microparticles, gas and volatile organic compounds (VOCs) sensors described hereafter. Indeed, these sensors are factory-calibrated to a known temperature and humidity level, but said sensors are generally sensitive to the climate conditions of the surrounding environment. The method continues with measurements of the concentration of volatile organic compounds (VOCs), of microparticles and of gases in the atmosphere of the electrical enclosure.

During a step 210, a measurement $MES_{VOC}$ of the concentration of volatile organic compounds (VOCs) is performed by means of a volatile organic compounds sensor 21, then a step 220 of correcting the measurement is performed to correct the measurement $MES_{VOC}$ performed in step 210 on the basis of the value of the one or more climate parameter(s) measured in step 100.

In an enclosure containing electrical equipment, there can be one or more equipment items 11, 12 diffusing volatile organic compounds during normal operation. The method of the invention is intended for the early detection of an abnormal emission of VOCs, following a fault in an equipment item 11, 12, surpassing a natural emission of VOCs from an equipment item 11, 12 during normal operation, i.e. without anomaly. To this end, during a step 230, the method performs a calculation of a mean $ML_{VOC}$ concentration of VOCs in the electrical enclosure 10 over a long period LP. Said mean concentration $ML_{VOC}$ reflects the level, during normal operation, of the concentration of VOCs inside the enclosure 10. In order to represent the normal operation of electrical equipment that is the size of an electrical enclosure, the long period LP preferably is between 5 and 12 hours. The long period LP can be adjusted on the basis of the thermal inertia of the equipment present in the enclosure and/or on the size of the enclosure 10.

Preferably, the mean concentration $ML_{VOC}$ over the long period is a running mean: the measurements $MES_{VOC}$ of the concentration of volatile organic compounds are performed at a fixed interval, preferably every 30 seconds. For a long period LP with a preferred duration of 8 hours, the mean concentration $ML_{VOC}$ over a long period will take into account 960 measurements $MES_{VOC}$. Any new measurement $MES_{VOC}$ replaces the oldest measurement, and a new mean calculation $ML_{VOC}$ over a long period is performed on the 960 most recent measurements $MES_{VOC}$.

For early detection of an abnormal emission of VOCs from an equipment item 11, 12, a running mean calculation $MC_{VOC}$ of the concentration of volatile organic compounds over a short period SP is performed during a step 240. Preferably, the duration of the short period is between 15 and 60 minutes. Thus, for a short period SP, the duration of which is equal to 30 minutes, due to a concentration measurement $MES_{VOC}$ preferably performed every 30 seconds, the mean calculation $MC_{VOC}$ over the short period will calculate a mean over the 60 most recent measurements $MES_{VOC}$. Subsequently, during a step 250, a calculation of the drift $DR_{VOC}$ of concentration of VOCs is performed. The drift of concentration of VOCs is equal to the ratio of the mean concentration $MC_{VOC}$ of VOCs over the short period to the mean concentration $ML_{VOC}$ of VOCs over the long period. Thus, the drift $DR_{VOC}$ is equal to $MC_{VOC}/ML_{VOC}$. The drift $DR_{VOC}$ of concentration of VOCs is compared, during step 260, to a predefined drift threshold $SD_{VOC}$. When the drift $DR_{VOC}$ is greater than $SD_{VOC}$, this involves an abnormal exceedance of the concentration of volatile organic compounds and a drift of concentration of VOCs alarm $ALD_{VOC}$ is emitted. Thus, any abnormal change of concentration of VOCs can be detected, in the case thus described, within the 30 minutes following the appearance of the fault. Preferably, the drift threshold $SD_{VOC}$ is between 1.001 and 1.10 (between 100.1% and 110% if the threshold is expressed as a percentage).

Figure 5:
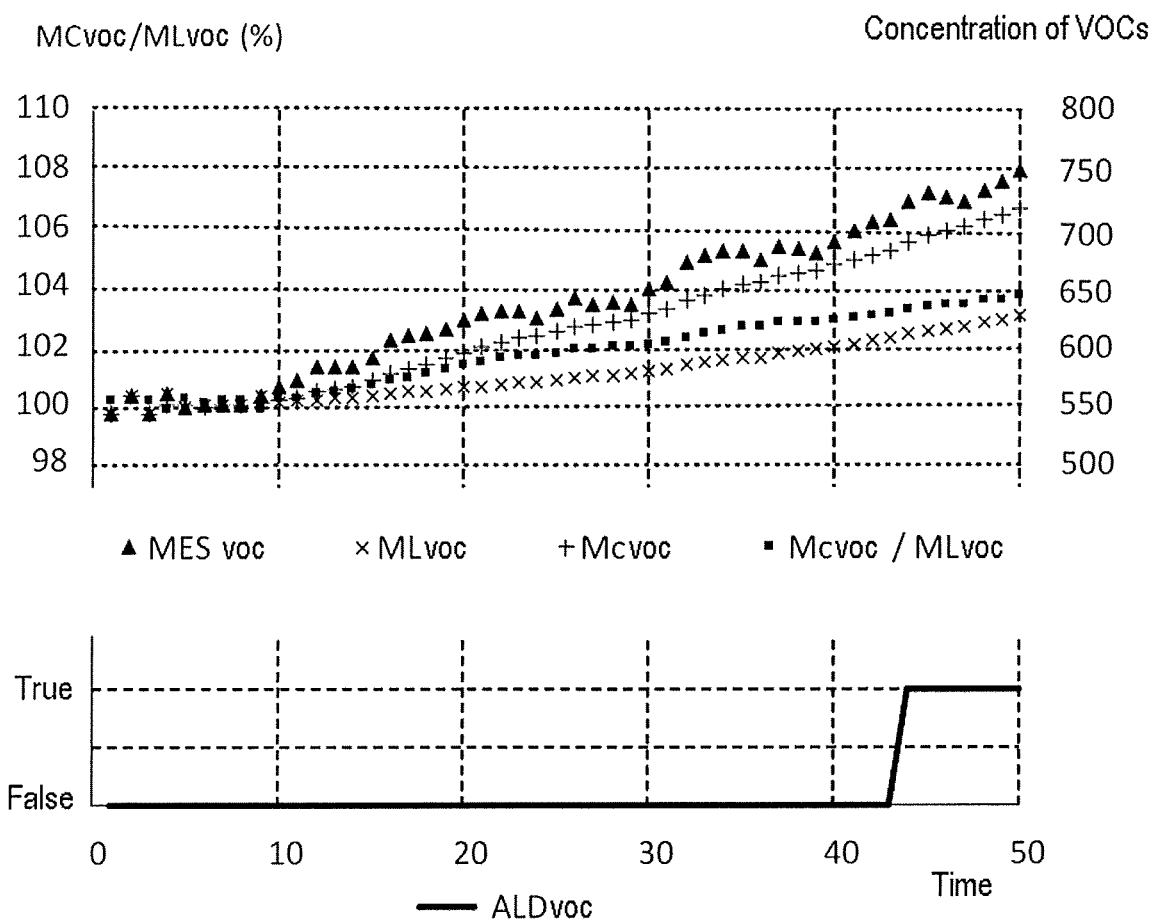
FIG. 5 is a graph showing measurements and results of calculations for showing an example of detecting a drift of concentration of volatile organic compounds that is greater than a predefined drift threshold.

FIG. 5 uses a graph to show an example of the detection of a drift of concentration of VOCs. The time unit corresponds to a 30 second period. A fault appears at the time t=10. The curve $MES_{VOC}$ represents the concentration values measured on the basis of time, the curve $ML_{VOC}$ represents the result of the calculation of the long period mean and $MC_{VOC}$ represents the result of the calculation of the short period mean. A scale of concentration is shown for these three curves on the right-hand axis of the graph. The curve $MC_{VOC}/ML_{VOC}$ represents the result of the drift calculation $DR_{VOC}$, expressed as a percentage on the left-hand axis of the graph. The drift $DR_{VOC}$ exceeds a predefined drift threshold $SD_{VOC}$ at the value of 1.03 (or 103%) at the time t=44 and an alarm $ALD_{VOC}$ is generated. Therefore, the fault was detected within a period of 34 measurement intervals, that is 17 minutes after the start of the fault when a measurement is performed every 30 seconds. The steps of calculating the drift of concentration of VOCs in the electrical enclosure allows the detection of a fault that is the source of a slowly developing release of VOCs in an atmosphere already comprising a concentration of VOCs that can be high at the normal rate.

The method is also intended to detect a fault that appears and develops quickly. To this end, a step 270 of calculating the change of emission of volatile organic compounds $EV_{VOC}$ is performed. $EV_{VOC}$ is calculated by calculating the difference between two consecutive measurements $MES_{VOC}$. Let $MES_{VOC}(t)$ be a measurement of $MES_{VOC}$ at the instant t and $MES_{VOC}(t+1)$ be a measurement of $MES_{VOC}$ at the instant t+1, then, at the instant t+1:

$$EV_{VOC}(t+1)=MES_{VOC}(t+1)-MES_{VOC}(t).$$

Figure 4:
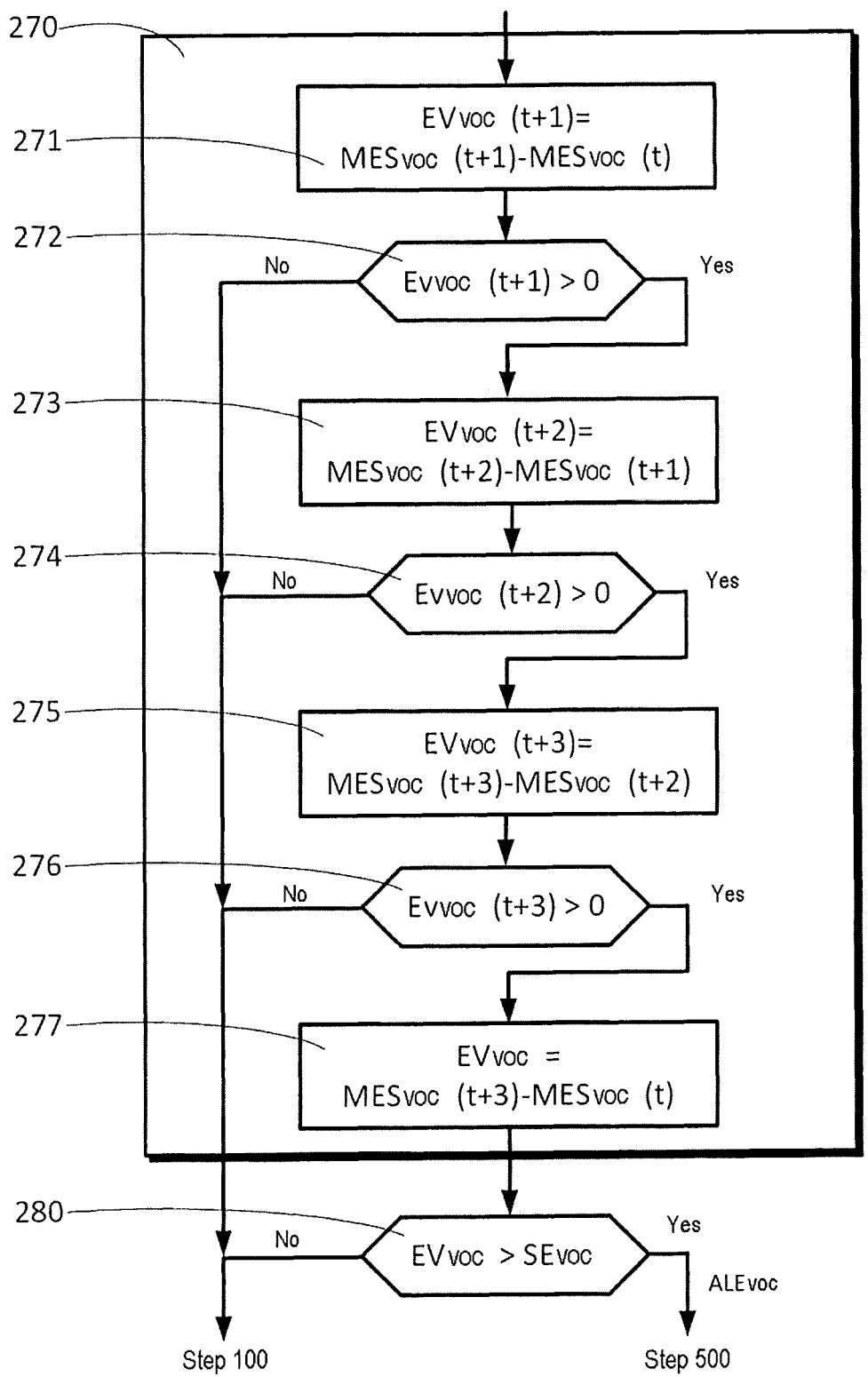
FIG. 4 shows a flow chart of part of the method shown in FIG. 1 for describing processing preferably used to quantify a change of concentration of microparticles.

The result of calculating the change of emission $EV_{VOC}(t+1)$ is compared, in step 280, to a predefined change of concentration threshold $SE_{VOC}$. When the result of calculating the change of emission $EV_{VOC}(t+1)$ is greater than the change threshold $SE_{VOC}$, then a change of concentration of VOCs alarm $ALE_{VOC}$ is emitted. When the value of $EV_{VOC}(t+1)$ is negative or is below the predefined change threshold $SE_{VOC}$, the method returns to the measurement 100 of climate parameters. In order to avoid a false alarm, it is worthwhile checking that the alarm is confirmed over several consecutive measurement cycles. According to a preferred embodiment, when all the results of calculating $EV_{VOC}$ are positive on 4 consecutive measurements of $EV_{VOC}$ and the difference between the last measurement $EV_{VOC}(t+3)$ performed at the instant t+3 and the first measurement $EV_{VOC}(t)$ performed at the instant t is greater than the threshold $SE_{VOC}$, then the change alarm $ALE_{VOC}$ is emitted. Such an iterative calculation is shown in FIG. 4 using a flow chart. The step 270 of calculating the change of emission of volatile organic compounds $EV_{VOC}$ begins with a step 271 of calculating the difference $EV_{VOC}(t+1)$ between the measurement $MES_{VOC}(t)$ at the instant t and the measurement $MES_{VOC}(t+1)$ at the instant (t+1). In step 272, if the change is positive, i.e. if $EV_{VOC}(t+1) > 0$, then the method continues with step 273. If $EV_{VOC}(t+1)$ is negative, the change is negative and there is no need to generate an alarm, the method returns to the step 100 of measuring climate parameters. In step 273, a calculation $EV_{VOC}(t+2)= MES_{VOC}(t+2)-MES_{VOC}(t+1)$ is performed. In step 274, if $EV_{VOC}(t+2) > 0$, then the method continues with step 275, otherwise the method returns to step 100. Steps 275 and 276 are similar to steps 273 and 274, but are applicable to the measurements $MES_{VOC}(t+3)$. Finally, in step 276, when $EV_{VOC}(t+3)$ is positive, the method has detected three positive consecutive changes of $EV_{VOC}$. A calculation of the difference $EV_{VOC}$ between the measurement $MES_{VOC}(t+3)$ at the instant (t+3) and the measurement $MES_{VOC}(t)$ at the instant t is performed. If $EV_{VOC}$ is greater than the change threshold $SE_{VOC}$, then a change of concentration of VOCs alarm $ALE_{VOC}$ is emitted. Other variations of calculating $EV_{VOC}$ can be used.

Preferably, the change threshold $SE_{VOC}$ is between 10 and 30 ppm.

Figure 6:
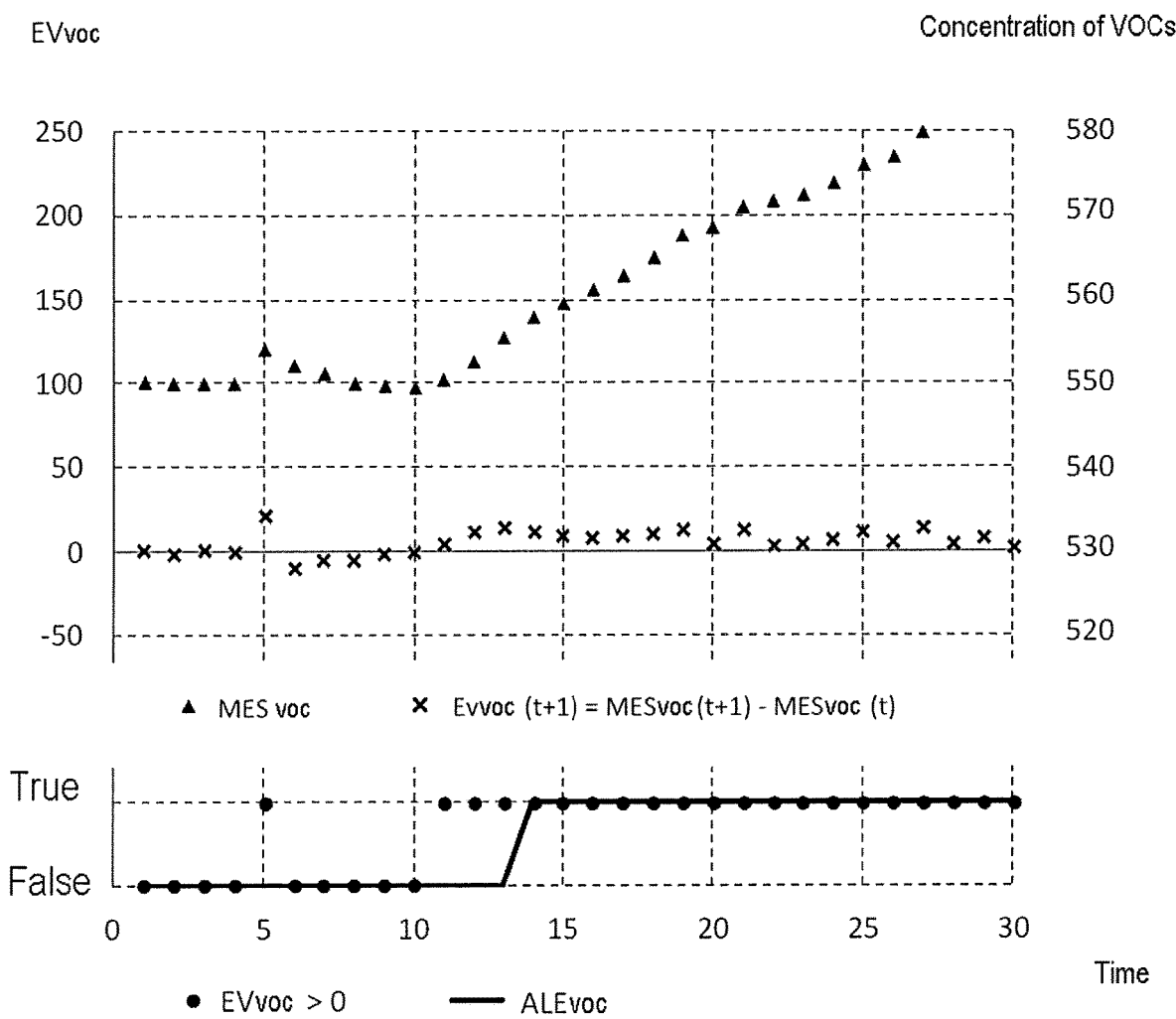
FIG. 6 is a graph showing measurements and results of calculations for showing an example of detecting a change that is greater than a predefined change of concentration threshold of volatile organic compounds.

FIG. 6 uses a graph to show an example of detecting an abnormal change of concentration of VOCs according to the preferred embodiment previously described.

The curve $MES_{VOC}$ represents the concentration values measured on the basis of time. A scale of concentration is shown on the right-hand axis of the graph. The curve $EV_{VOC}$ represents the difference between two consecutive measurements $MES_{VOC}$. A scale on the left-hand side of the graph corresponds to the curve $EV_{VOC}$. The curve $EV_{VOC} > 0$ indicates all the occurrences where the difference in value between two consecutive measurements is positive. At the time t=5, the difference between two consecutive measurements is positive, but the phenomenon did not occur, therefore the alarm was not generated. However, from t=10, four positive consecutive exceedances occurred and the threshold $SE_{VOC}$ was exceeded, an alarm $ALE_{VOC}$ is therefore emitted. The fault that quickly developed was therefore detected within a period of 4 measurement intervals after the start of the fault, that is 2 minutes when the interval between two measurements is 30 seconds.

Figure 2:
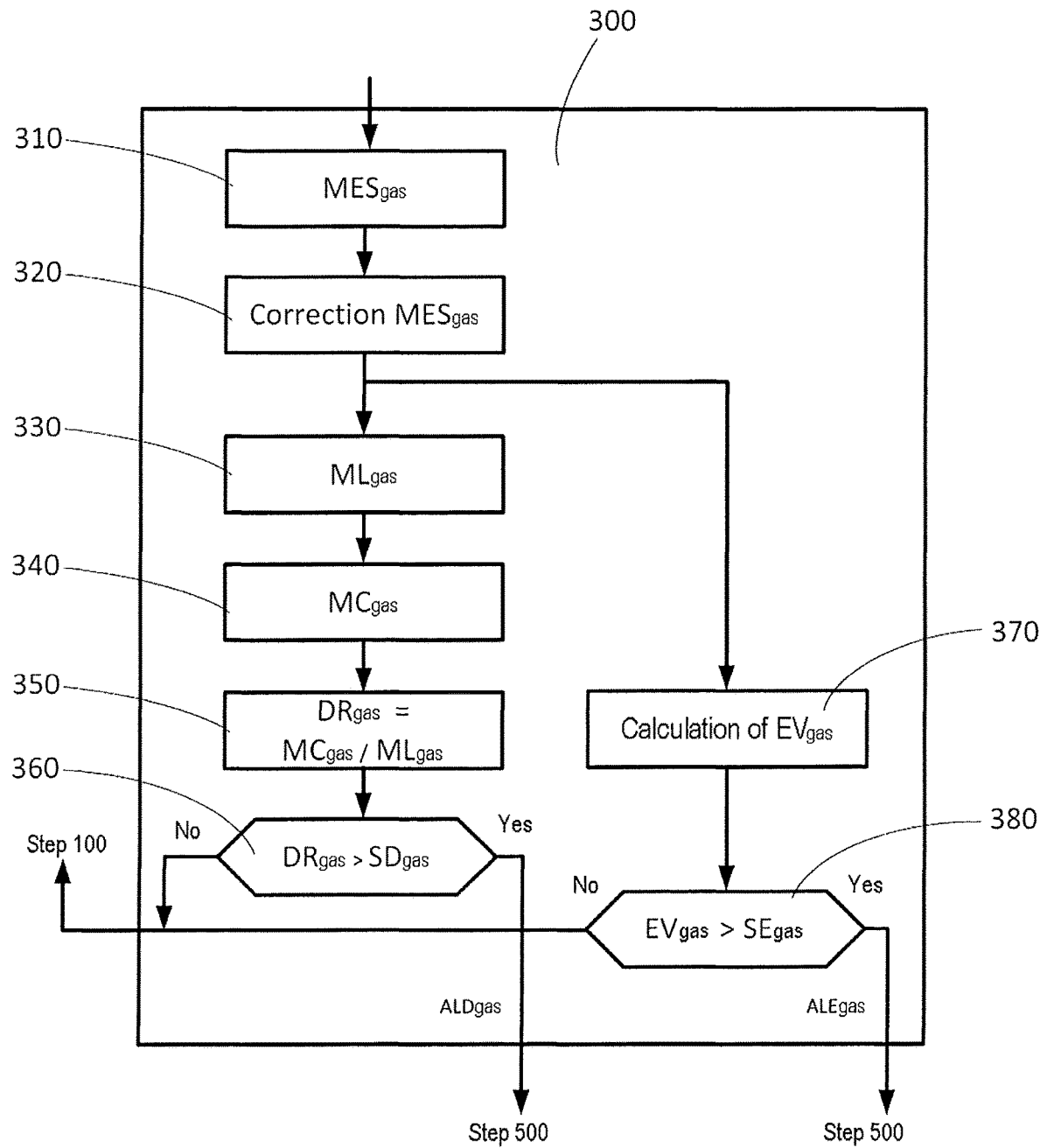
FIG. 2 shows a flow chart of part of the method shown in FIG. 1 for describing processing of the gas concentration measurement.

The set of steps 210 to 280 of measuring the concentration of volatile organic compounds (VOCs) and of detecting the exceedance of the drift $SD_{VOC}$ or change $EV_{VOC}$ of concentration threshold forms part of a first method 200 for measuring the concentration of volatile organic compounds (VOCs). A second method 300 for measuring the concentration of gases is also executed. The second method 300 is shown in the flow chart of FIG. 1 and is shown in detail in FIG. 2. The second method 300 comprises steps similar to the first method 200. A step 310 of measuring $MES_{gas}$ of the concentration of gases is performed, followed by a step 320 of correcting the measurement $MES_{gas}$ on the basis of the one or more climate parameter(s) measured in step 100. Subsequently, a step 330 is performed of calculating a running mean $ML_{gas}$ of the concentration of gases in the electrical enclosure 10 over the long period LP, then a step 340 is performed of calculating a running mean $MC_{gas}$ over the short period SP. A calculation of a drift $DR_{gas}$ of concentration of gases equal to the ratio $MC_{gas}/ML_{gas}$ is performed during a step 350, then the drift calculation $DR_{gas}$ is compared to a drift of concentration threshold $SD_{gas}$ of gases in step 360. When the drift of concentration threshold $SD_{gas}$ of gases is exceeded, a drift of concentration of gases alarm $ALD_{gas}$ is emitted. In order to detect a quickly developing release of gases, a calculation of the change $EV_{gas}$ of concentration of gases is performed according to steps similar to the calculation of the change of VOCs: during a step 370, a calculation of the change of concentration of gases between two consecutive instants t and t+1 is performed according to the equation $EV_{gas}(t+1)=MES_{gas}(t+1)-MES_{gas}(t)$. In step 380, the value of $EV_{gas}(t+1)$ is compared to a predefined change threshold $SE_{gas}$. When the value $EV_{gas}(t+1)$ is greater than the threshold $SE_{gas}$, then an abnormal change of concentration of gases alarm $ALE_{gas}$ is emitted. When the value of $EV_{gas}(t+1)$ is negative or is below the predefined change threshold $SE_{gas}$, the method returns to the measurement 100 of climate parameters. Preferably, the calculation of the change $EV_{gas}$ of concentration of gases is performed according to a method similar to the calculation of the change of concentration of VOCs based on four positive consecutive measurements. Preferably, the drift threshold $SD_{gas}$ is between 1.001 and 1.1 (between 100.1% and 110% expressed as a percentage) and the change threshold $SE_{gas}$ is between 5 and 50 ppm.

Figure 3:
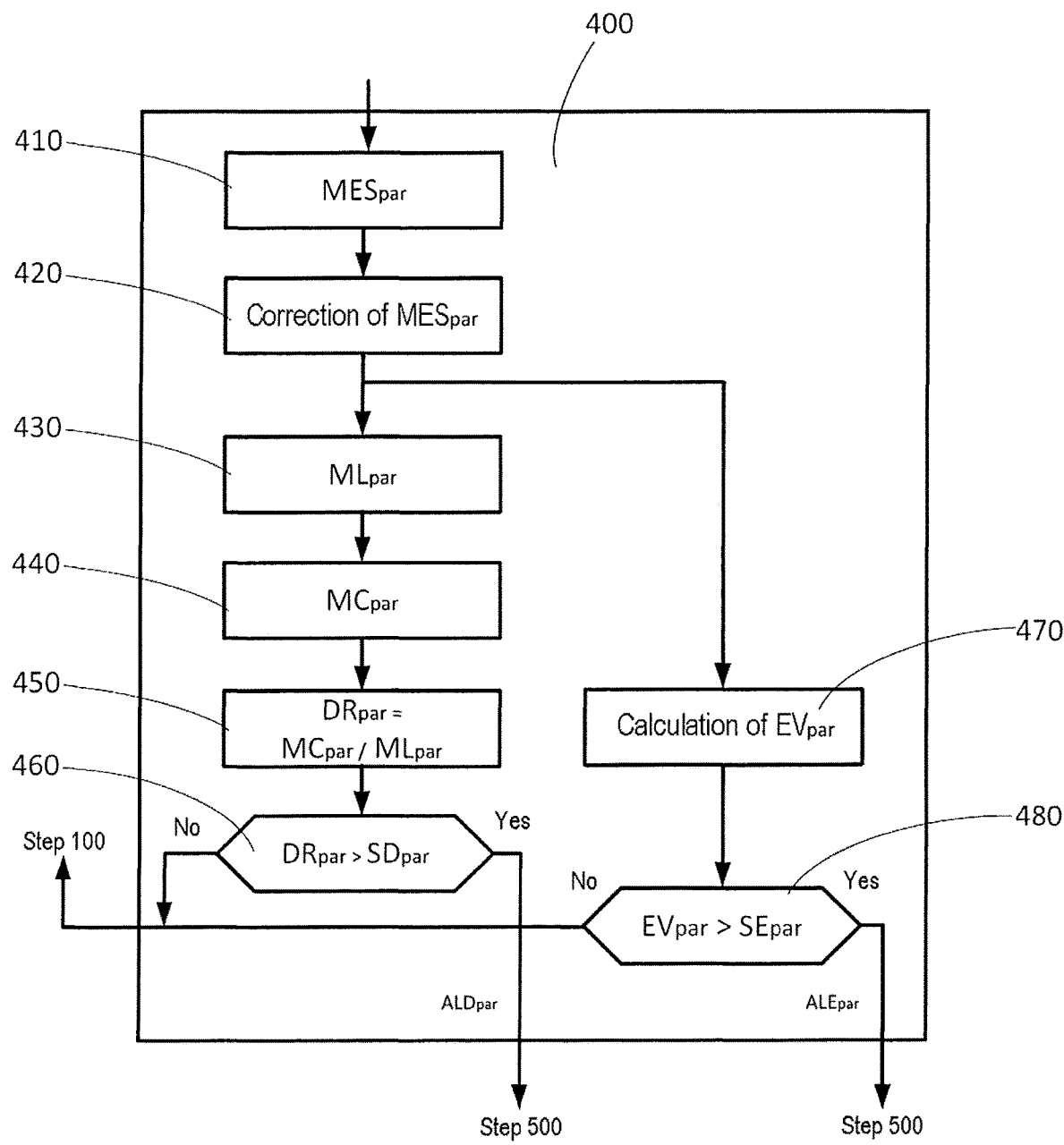
FIG. 3 shows a flow chart of part of the method shown in FIG. 1 for describing processing of the microparticles concentration measurement.

Similarly, the fault detection method according to the invention comprises a third method 400 intended to generate an alarm in the event of an abnormal drift or change of concentration of microparticles in the electrical enclosure. The third method 400 for measuring the concentration of microparticles is shown in the flow chart of FIG. 1 and is shown in detail in FIG. 3. The third method 400 comprises steps similar to the first method 200 and to the second method 300. A step 410 of measuring $MES_{par}$ the concentration of microparticles is performed, then the measurement $MES_{par}$ is corrected on the basis of the one or more climate parameter(s) measured in step 100, during a step 420. A calculation of a running mean $ML_{par}$ of the concentration of microparticles in the electrical enclosure 10 is performed over the long period LP during a step 430 and a running mean $MC_{par}$ is calculated over the short period SP during a step 440. A calculation of a drift $DR_{par}$ of the concentration of microparticles equal to the ratio $MC_{par}/ML_{par}$ is performed in a step 450 and the result of the drift calculation $DR_{par}$ is compared to a predefined drift of microparticles threshold $SD_{par}$ during a step 460. When the drift of concentration of microparticles threshold $SD_{par}$ is exceeded, a drift of concentration of microparticles alarm $ALD_{par}$ is emitted. If the value of the drift $DR_{par}$ is below the predefined change threshold $SD_{par}$, the method returns to the measurement 100 of climate parameters. A calculation of the change $EV_{par}$ of concentration of microparticles is also performed: during a step 470, a calculation of the change of concentration of microparticles is performed according to the equation $EV_{par}(t+1)=MES_{par}(t+1)-MES_{par}-(t)$. In the step 480, the value $EV_{par}$ is compared to a predefined change threshold $SE_{par}$ in order to generate an alarm $ALE_{par}$ when the result of the calculation of the change $EV_{par}$ of concentration of microparticles is greater than the change threshold $SE_{par}$. When the value of $EV_{par}$ is negative or is below the change threshold $SE_{par}$, the method returns to the measurement 100 of climate parameters. Preferably, the calculation of the change $EV_{par}$ of concentration of microparticles is performed according to a method similar to the calculation of the concentration of VOCs based on four positive consecutive measurements. Preferably, the drift threshold $SD_{par}$ is between 1 and 100 µg/m³ and the change threshold $SE_{par}$ is between 20 and 150 µg/m³.

The emissions of volatile organic compounds, of microparticles or of gases are associated with the operation of the electrical equipment present in the electrical enclosure and are not necessarily a fault indicator. A feature of the invention is the provision of a reliable alarm relating to a fault in equipment during operation in a clean equipment environment. To this end, the detection method of the invention comprises a step 500 of concentrating alarm information, during which an "AND" logical operation is performed between alarms of VOCs, of microparticles and of gases. A feature of the invention is the generation of an alarm if at least one warning of the concentration of microparticles is triggered and if at least one warning of the concentration of VOCs or of gases is triggered. As shown in FIG. 1, on the one hand, under reference sign 510, an "OR" logical operation of the warnings of drift and of change for the VOCs and the gases is performed, on the other hand, under reference sign 520, an "OR" logical operation of the warnings of drift and of change of concentration of microparticles is performed. An "AND" logical operation, under reference sign 530, is performed between the warning of the exceedance of microparticles and a warning of the exceedance of gases or of VOCs. A logical equation for generating an alarm variable AL is expressed as:

$$AL=(ALD_{par} \text{ OR } ALE_{par}) \text{ AND } (ALD_{VOC} \text{ OR } ALE_{VOC} \text{ OR } ALD_{gas} \text{ OR } ALE_{gas}).$$

When the alarm variable AL is true, an alarm is generated during step 600. The operator of the electrical installation can quickly intervene and resolve the fault.

By way of an illustration of the benefit of the method, a clamped poor connection of a low-power cable on a terminal can result in a temperature rise beyond the specification of the insulating material of the cable. The overheated insulating material will emit VOCs, gases and microparticles. Furthermore, high-power cables, in which high currents circulate, also can be present in the enclosure. The insulating materials of the high-power cables emit, during normal operation, VOCs, gases and microparticles at quantities that can be much greater than those emitted by the overheating low-power cable. The steps of calculating the drift of concentration of VOCs, of microparticles and of gases will allow the detection of a positive and abnormal variation of the concentration of VOCs, of gases and of microparticles compared to a level corresponding to normal operation. A possible thermal runaway in the vicinity of the low-power cable will be quickly detected during the steps of calculating the change of concentration. A combined exceedance of the thresholds of concentration of VOCs, of microparticles and of gases allows an alarm to be generated only when there is an actual fault. Such a method also allows a fault to be detected, such as an abnormal electric arc in the electrical enclosure 10, by virtue of the detection of the VOCs, the microparticles and the gases, in particular the ozone, emitted by the materials subject to the effects of the electric arc.

The method of the invention is executed cyclically in order to ensure continuous monitoring of the equipment in the electrical enclosure 10 and to detect any abnormal change of VOCs, of gases or of microparticles as quickly as possible. The interval between two consecutive cycles can be between a few seconds and several minutes. Preferably, said interval is equal to 30 seconds.

Figure 7:
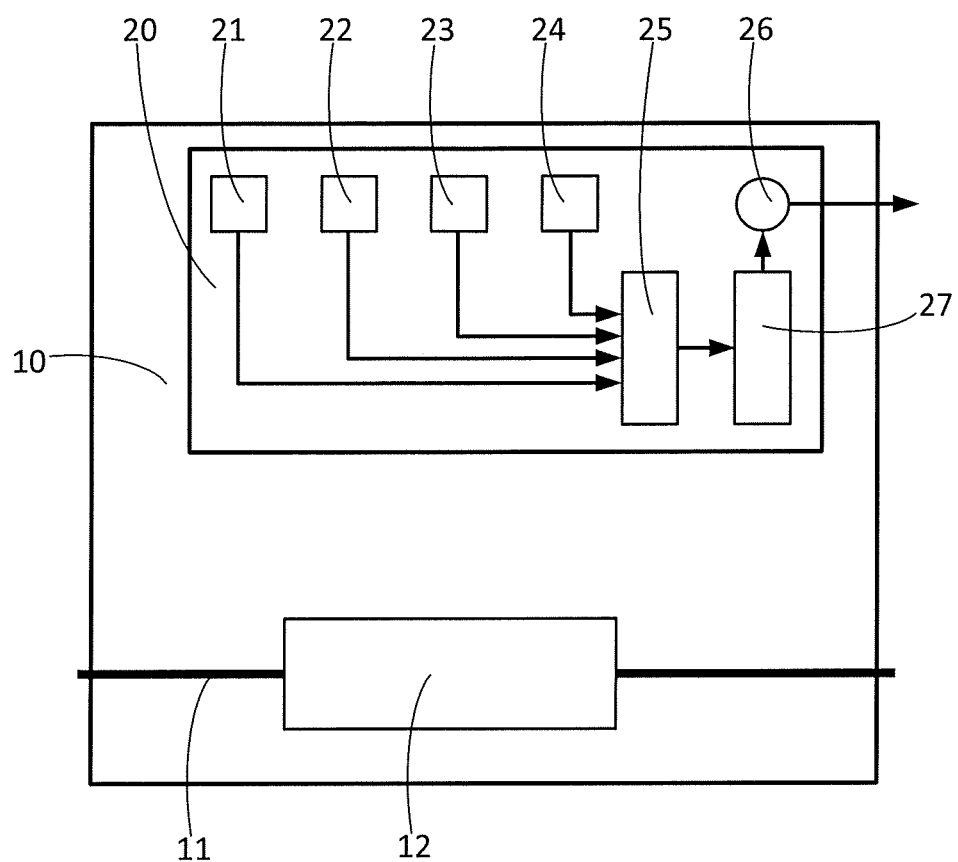
FIG. 7 is a block diagram of an electrical enclosure comprising at least one cable or one electrical equipment item and a device for detecting an electrical fault according to the invention.

The invention also relates to a device 20, shown in FIG. 7, for detecting a fault in an electrical enclosure 10. The detection device 20 comprises:
- at least one sensor 21 for supplying a signal characteristic of the concentration of volatile organic compounds;
- at least one sensor 22 for supplying a signal characteristic of the concentration of microparticles;
- at least one sensor 23 for supplying a signal characteristic of the concentration of gases;

at least one climate parameter sensor 24;

a measurement circuit 25 for measuring the signals supplied by the sensors;

an alarm circuit 26 for generating an alarm; and a processing unit 27 comprising circuits for executing the method for detecting a fault as previously described and for activating the alarm circuit 26 when the drift of concentration threshold $SD_{par}$ of microparticles or the change of concentration threshold $EV_{par}$ of microparticles is exceeded, and when at least one drift of concentration threshold or one change of concentration threshold of volatile organic compounds $SD_{VOC}$, $EV_{VOC}$ or of gases $SD_{gas}$, $EV_{gas}$ is exceeded. The processing unit can simultaneously execute the first 200, second 300 and third 400 methods for detecting exceedance of the drift or change of concentration threshold by means of calculation units, such as microprocessors operating in parallel or sequentially, one after the other if there is only one calculating unit in the processing unit 27. Any calculating means, such as a controller, an assembly of logical and/or analogue electronic circuits, can be used. The method of the invention is executed cyclically by the processing unit, preferably with a period of 30 seconds. According to a preferred embodiment, the sensors are calibrated when the detection device 20 is manufactured and temperature and humidity correction curves for the signals supplied by the VOC 21, microparticles 22 and gas 23 sensors are stored in the processing unit 27 for executing the steps 220, 320, 420 of correcting measurements of the concentration of volatile organic compounds $MES_{VOC}$, of gases $MES_{gas}$ and of microparticles $MES_{par}$. The climate parameters sensor 24 preferably is a temperature and humidity sensor. Other sensors 24 can be added to measure other climate parameters, for example, the atmospheric pressure, inside or in the vicinity of the electrical enclosure 10.

The volatile organic compounds preferably detected by the sensor 21 are made up of or comprise molecules of hydrocarbon or alcohol, benzene, ethanol, propane, isobutane, T-butanol or even of 2-butanone. A VOCs sensor 21 can be produced by associating a plurality of specific sensors with certain types of VOCs and supplying a signal characteristic of the total concentration of volatile organic compounds. A plurality of sensors also can be used and, in this case, the measurement circuit 25 performs a sum, which is possibly weighted, of the signals emitted by each sensor in order to produce the measurement $MES_{VOC}$.

The microparticles sensor 22 preferably detects any microparticles of between 1 and 5 microns that are emitted by the one or more insulating materials of the electrical cables.

A microparticles sensor 22 can be produced by associating a plurality of specific sensors with certain types of microparticles and supplying a signal characteristic of the total concentration of microparticles. A plurality of sensors also can be used and, in this case, the measurement circuit 25 performs a sum, which is possibly weighted, of the signals emitted by each sensor in order to produce the measurement $MES_{par}$.

The gases preferably detected by the gas sensor 23 are:
ammonia;
hydrogen;
acetone;
ozone.

A gas sensor 23 can be produced by associating a plurality of specific sensors with certain gases and supplying a signal characteristic of the total concentration of gases. A plurality of sensors also can be used and, in this case, the measurement circuit 25 performs a sum, which is possibly weighted, of the signals emitted by each sensor in order to produce the measurement $MES_{gas}$.

The invention also relates to an electrical enclosure 10 comprising at least one cable or one electrical equipment item 11, 12 and a device 20 for detecting an electrical fault for detecting an abnormal temperature rise of a cable or an electrical equipment item 11, 12. The alarm generated by the alarm circuit 26 preferably is emitted by means of a light and/or audible warning device in the vicinity of the electrical enclosure 10 and can be simultaneously transmitted by wired or radio means to a remote monitoring station, not shown in FIG. 7. Thus notified, a member of personnel can quickly intervene to remove the cause of the fault.

The invention claimed is:

1. A method for detecting a fault in an electrical enclosure comprising at least one electrical equipment item and at least one volatile organic compounds (VOCs) sensor, at least one microparticles sensor, at least one gas sensor, wherein said method comprises cyclically performing:

measuring at least one climate parameter in the electrical enclosure;

measuring a concentration of VOCs;

measuring a concentration of gases;

measuring a concentration of microparticles;

correcting the measurements of the concentration of the VOCs, the concentration of the gases, and the concentration of the microparticles based on the measured at least one climate parameter;

calculating a drift of concentration of the VOCs, a drift concentration of the gases, and a drift concentration of the microparticles as a function of time;

comparing the drift of concentration of the VOCs, the drift concentration of the gases and the drift concentration of the microparticles, respectively, to a predefined drift threshold of VOCs, a predefined drift threshold of gases, and a predefined drift threshold of microparticles;

calculating a change of concentration of the VOCs, a change of concentration of the gases, and a change of concentration of the microparticles;

comparing the change of concentration of the VOCs, the change of concentration of the gases, and the change of concentration of the microparticles, respectively, to a predefined change threshold of VOCs, a predefined change threshold of gases, and a predefined change threshold of microparticles;

emitting an alarm when both of the following are true:
  (1) the drift concentration threshold of microparticles or the change concentration threshold of microparticles is exceeded; and
  (2) at least one of the drift threshold of VOCs, the drift threshold of gases, the change threshold of VOCs, and the change threshold of gases is exceeded.

2. The method for detecting the fault in the electrical enclosure according to claim 1, wherein the step of calculating the drift concentration of the VOCs, the drift concentration of the gases, and the drift concentration of the microparticles comprises:

calculating a first running mean, over a first predetermined period, of the concentration of the VOCs, the concentration of the gases, and the concentration of the microparticles;

calculating a second running mean, over a second predetermined period shorter than the first predetermined period, of the concentration of the VOCs, the concentration of the gases, and the concentration of the microparticles;

calculating a ratio respectively between the second running mean and the first running mean.

3. The method for detecting the fault in the electrical enclosure according to claim 2, wherein the second predetermined period is between 15 and 60 minutes and the first predetermined period is between 5 and 12 hours.

4. The method for detecting the fault in the electrical enclosure according to claim 1, wherein the step of calculating the change of concentration of the VOCs, the change of concentration of the gases, and the change of concentration of the microparticles comprises at least one calculation of a difference between two consecutive measurements of, respectively, the measured concentration of the VOCs, the measured concentration of the gases, and the measured concentration of the microparticles.

5. A device for detecting the electrical fault comprising:
the at least one VOC sensor to supply a signal characteristic of the concentration of the VOCs;
the at least one microparticle sensor to supply a signal characteristic of the concentration of the microparticles;
the at least one gas sensor to supply a signal characteristic of the concentration of the gases;
at least one climate parameter sensor to supply a value of the at least one climate parameter;
a measurement circuit to measure the signals supplied by the sensors;
an alarm circuit configured to generate the alarm; and
processing circuitry,
wherein the processing circuitry is configured to execute the method for detecting the fault according to claim 1, and to activate the alarm circuit.

6. The device for detecting the electrical fault according to claim 5, wherein the at least one gas sensor is configured to supply a signal characterizing a concentration of ammonia.

7. The device for detecting the electrical fault according to claim 5, wherein the at least one gas sensor is configured to supply a signal characterizing a concentration of ozone.

8. The device for detecting the electrical fault according to claim 5, wherein the VOC sensor is configured to supply a signal characterizing a concentration of hydrocarbons.

9. The device for detecting the electrical fault according to claim 5, wherein the at least one climate parameter sensor is configured to supply a signal characterizing a temperature in the electrical enclosure.

10. The device for detecting the electrical fault according to claim 9, wherein the at least one climate parameter sensor is further configured to supply a signal characterizing humidity in the electrical enclosure.

11. An electrical enclosure comprising at least one cable or one electrical equipment item, the electrical enclosure comprising the device for detecting the electrical fault according to claim 5.

* * * * *